US011017116B2

(12) United States Patent
Riddle et al.

(10) Patent No.: US 11,017,116 B2
(45) Date of Patent: May 25, 2021

(54) SECURE INTEGRATION OF DIAGNOSTIC DEVICE DATA INTO A WEB-BASED INTERFACE

(71) Applicant: Onsite Health Diagnostics, LLC., Coppell, TX (US)

(72) Inventors: Jon Riddle, Mansfield, TX (US); Steve Staneff, Flower Mound, TX (US)

(73) Assignee: ONSITE HEALTH DIAGNOSTICS, LLC, Coppell, TX (US)

( * ) Notice: Subject to any disclaimer, the term of this patent is extended or adjusted under 35 U.S.C. 154(b) by 302 days.

(21) Appl. No.: 15/941,077

(22) Filed: Mar. 30, 2018

(65) Prior Publication Data

US 2019/0303609 A1   Oct. 3, 2019

(51) Int. Cl.
| | | |
|---|---|---|
| *G06F 21/06* | (2006.01) | |
| *G06F 21/62* | (2013.01) | |
| *G06F 9/54* | (2006.01) | |
| *G16H 10/40* | (2018.01) | |

(52) U.S. Cl.
CPC .......... *G06F 21/6245* (2013.01); *G06F 9/547* (2013.01); *G06F 21/629* (2013.01); *G16H 10/40* (2018.01)

(58) Field of Classification Search
CPC .... G06F 21/6245; G06F 9/547; G06F 21/629; G16H 10/40
USPC ........................................................ 726/30
See application file for complete search history.

(56) References Cited

U.S. PATENT DOCUMENTS

| 5,883,985 | A | * | 3/1999 | Pourjavid | ............... | H04L 29/06 |
| | | | | | | 345/20 |
| 6,557,102 | B1 | * | 4/2003 | Wong | ..................... | G06F 21/00 |
| | | | | | | 713/176 |
| 7,106,479 | B2 | * | 9/2006 | Roy | ....................... | G06F 19/321 |
| | | | | | | 358/3.27 |
| 10,229,100 | B1 | * | 3/2019 | Lesner | ..................... | G06T 11/00 |
| 10,769,363 | B2 | * | 9/2020 | Leitner | ................ | G06F 40/186 |
| 2001/0049610 | A1 | * | 12/2001 | Hazumi | ................. | G06Q 10/10 |
| | | | | | | 705/3 |
| 2002/0029157 | A1 | * | 3/2002 | Marchosky | ............ | G16H 40/67 |
| | | | | | | 705/3 |
| 2002/0038227 | A1 | * | 3/2002 | Fey | ........................ | G06Q 50/24 |
| | | | | | | 705/3 |
| 2002/0124177 | A1 | * | 9/2002 | Harper | ................ | G06F 21/6245 |
| | | | | | | 713/189 |

(Continued)

*Primary Examiner* — Shahriar Zarrineh
(74) *Attorney, Agent, or Firm* — Clayton, McKay & Bailey, PC

(57) ABSTRACT

A method of securely integrating device data from an external device with a user device may include implementing a local data call function of a remote application through a native application of the user device such that the remote application receives device data without the device data being permanently stored on the user device; validating the device data with the remote application according to data elements of the device data and a first set of local fields; requesting a first authorization to integrate the device data; associating a first data control element with the data elements according to a first request result; requesting a second authorization to integrate the device data; and populating storage fields that are maintained by a backend and associated with the first control data element, with the data elements according to a second request result.

20 Claims, 8 Drawing Sheets

(56) References Cited

U.S. PATENT DOCUMENTS

| | | | |
|---|---|---|---|
| 2002/0133373 A1* | 9/2002 | Silva-Craig | G06F 19/321 705/2 |
| 2002/0169637 A1* | 11/2002 | Akers | G06F 19/3418 705/3 |
| 2003/0014284 A1* | 1/2003 | Jones | G06Q 30/02 705/3 |
| 2003/0206646 A1* | 11/2003 | Brackett | G06F 19/321 382/128 |
| 2004/0071038 A1* | 4/2004 | Sterritt | G06F 19/321 365/232 |
| 2004/0117215 A1* | 6/2004 | Marchosky | G16H 10/60 705/3 |
| 2005/0114179 A1* | 5/2005 | Brackett | G06Q 10/10 705/2 |
| 2005/0120300 A1* | 6/2005 | Schwager | G06Q 50/24 715/201 |
| 2005/0240445 A1* | 10/2005 | Sutherland | G06F 19/321 705/3 |
| 2005/0275871 A1* | 12/2005 | Baird | H04L 12/2854 358/1.15 |
| 2006/0195339 A1* | 8/2006 | Backhaus | G06Q 10/06 705/2 |
| 2006/0212484 A1* | 9/2006 | Chaffin, Jr. | G16H 10/60 |
| 2006/0230072 A1* | 10/2006 | Partovi | G06Q 10/06 |
| 2006/0242159 A1* | 10/2006 | Bishop | G06F 19/321 |
| 2007/0052734 A1* | 3/2007 | Skinner, Jr. | G06T 19/00 345/689 |
| 2007/0129967 A1* | 6/2007 | Thompson | G06Q 50/22 705/2 |
| 2007/0167713 A1* | 7/2007 | Fukatsu | G06F 19/321 600/407 |
| 2007/0179811 A1* | 8/2007 | Reiner | G06F 19/321 705/2 |
| 2007/0192140 A1* | 8/2007 | Gropper | G16H 10/60 705/3 |
| 2007/0234219 A1* | 10/2007 | Bhattaru | G16H 40/63 715/744 |
| 2008/0120142 A1* | 5/2008 | Jakobovits | G06Q 50/24 705/3 |
| 2008/0133273 A1* | 6/2008 | Marshall | G16H 40/67 705/3 |
| 2008/0221929 A1* | 9/2008 | Brackett | G06F 19/321 705/3 |
| 2008/0247676 A1* | 10/2008 | Minakuchi | G16H 15/00 382/305 |
| 2009/0006850 A1* | 1/2009 | Birger | H04L 29/12207 713/169 |
| 2009/0037334 A1* | 2/2009 | Hsu | G06Q 10/10 705/51 |
| 2009/0112882 A1* | 4/2009 | Maresh | G06F 19/321 |
| 2009/0132285 A1* | 5/2009 | Jakobovits | G06F 3/0482 705/3 |
| 2009/0164253 A1* | 6/2009 | Lyshkow | G06F 19/321 705/3 |
| 2009/0274384 A1* | 11/2009 | Jakobovits | G06F 16/51 382/254 |
| 2009/0313170 A1* | 12/2009 | Goldner | G06F 21/6254 705/50 |
| 2010/0030690 A1* | 2/2010 | Herlitz | G06F 21/6245 705/50 |
| 2010/0100848 A1* | 4/2010 | Ananian | G06F 3/0482 715/834 |
| 2010/0246981 A1* | 9/2010 | Hu | G06F 19/321 382/232 |
| 2010/0299157 A1* | 11/2010 | Fram | G06Q 50/24 705/3 |
| 2011/0022414 A1* | 1/2011 | Ge | G06Q 10/00 705/3 |
| 2011/0075897 A1* | 3/2011 | Dekel | H04N 19/63 382/128 |
| 2011/0119088 A1* | 5/2011 | Gunn | G06Q 50/24 705/3 |
| 2011/0153351 A1* | 6/2011 | Vesper | G06Q 50/22 705/2 |
| 2011/0213889 A1* | 9/2011 | Krotz | G06F 19/321 709/228 |
| 2011/0282844 A1* | 11/2011 | Bates | G06F 19/321 707/661 |
| 2012/0029303 A1* | 2/2012 | Shaya | A61B 5/0022 600/300 |
| 2012/0041786 A1* | 2/2012 | Yu | G06Q 50/24 705/3 |
| 2012/0084350 A1* | 4/2012 | Xie | G06F 9/5088 709/203 |
| 2012/0158882 A1* | 6/2012 | Oehme | G06F 16/1858 709/213 |
| 2012/0162401 A1* | 6/2012 | Melder | H04N 7/183 348/65 |
| 2012/0173317 A1* | 7/2012 | Kelley | G06Q 30/0241 705/14.4 |
| 2012/0179908 A1* | 7/2012 | Duma | G16H 10/65 713/165 |
| 2012/0221535 A1* | 8/2012 | Dubbels | G06F 16/27 707/694 |
| 2012/0250990 A1* | 10/2012 | Bocirnea | G06T 3/4015 382/166 |
| 2012/0266251 A1* | 10/2012 | Birtwhistle | H04W 12/003 726/26 |
| 2012/0269412 A1* | 10/2012 | Guan | G06T 1/0028 382/128 |
| 2013/0080414 A1* | 3/2013 | Dudala | G16H 40/20 707/706 |
| 2013/0129048 A1* | 5/2013 | Chicchetti | H05G 1/08 378/62 |
| 2013/0151286 A1* | 6/2013 | Kablotsky | G06F 19/321 705/3 |
| 2013/0185331 A1* | 7/2013 | Conemac | G06F 16/27 707/783 |
| 2013/0297345 A1* | 11/2013 | Curry | G16H 10/60 705/3 |
| 2013/0311201 A1* | 11/2013 | Chatfield | G16H 50/20 705/3 |
| 2014/0010421 A1* | 1/2014 | Colaco | G06F 16/182 382/128 |
| 2014/0073880 A1* | 3/2014 | Boucher | A61B 1/04 600/301 |
| 2014/0082111 A1* | 3/2014 | Schneider | G06Q 10/00 709/206 |
| 2014/0123237 A1* | 5/2014 | Gaudet | H04L 63/08 726/4 |
| 2014/0133632 A1* | 5/2014 | Wakai | A61B 5/00 378/98 |
| 2014/0142982 A1* | 5/2014 | Janssens | G06F 19/321 705/3 |
| 2014/0142984 A1* | 5/2014 | Wright | G06F 19/321 705/3 |
| 2014/0149512 A1* | 5/2014 | Leitch | H04L 67/1061 709/204 |
| 2014/0164948 A1* | 6/2014 | Joo | G06F 19/321 715/752 |
| 2015/0058042 A1* | 2/2015 | Vrbicky | G06F 19/321 705/3 |
| 2015/0080655 A1* | 3/2015 | Peterson | A61B 1/00009 600/112 |
| 2015/0149565 A1* | 5/2015 | Ahmed | H04L 65/403 709/206 |
| 2015/0193579 A1* | 7/2015 | Bruce | G06F 19/321 705/2 |
| 2015/0213218 A1* | 7/2015 | Ishii | G06Q 50/22 705/3 |
| 2015/0261917 A1* | 9/2015 | Smith | G06F 21/6263 705/3 |
| 2015/0264015 A1* | 9/2015 | Cialdea | G06F 19/321 726/26 |
| 2015/0347682 A1* | 12/2015 | Chen | G16H 50/30 705/2 |
| 2015/0379198 A1* | 12/2015 | Tambasco, Jr. | G16H 10/60 705/3 |

(56) References Cited

U.S. PATENT DOCUMENTS

| | | | |
|---|---|---|---|
| 2015/0381617 A1* | 12/2015 | Jung | H04W 12/08 455/411 |
| 2016/0004820 A1* | 1/2016 | Moore | H04W 4/21 705/3 |
| 2016/0012739 A1* | 1/2016 | Jafari | G09B 5/06 434/353 |
| 2016/0055589 A1* | 2/2016 | Billings | G06Q 40/08 705/4 |
| 2016/0085934 A1* | 3/2016 | Govaerts | A61B 6/461 378/98.5 |
| 2016/0125152 A1* | 5/2016 | Higgs | G06F 19/3418 705/3 |
| 2016/0147428 A1* | 5/2016 | De Sallier Dupin | G06F 3/04883 715/735 |
| 2016/0147944 A1* | 5/2016 | Douglass | G06F 21/31 705/51 |
| 2016/0147952 A1* | 5/2016 | Garcia | G16H 10/60 705/3 |
| 2016/0246788 A1* | 8/2016 | Thangaraj | G06F 16/51 |
| 2016/0267222 A1* | 9/2016 | Larcom | G06F 19/321 |
| 2016/0283656 A1* | 9/2016 | Charlot | G16H 40/20 |
| 2017/0091385 A1* | 3/2017 | Knoplioch | H04L 67/1097 |
| 2017/0161439 A1* | 6/2017 | Raduchel | G06Q 10/063 |
| 2017/0206322 A1* | 7/2017 | Kumar | G06Q 50/24 |
| 2017/0208047 A1* | 7/2017 | Rosenberg | G16H 50/70 |
| 2017/0208064 A1* | 7/2017 | Rosenberg | G16H 50/70 |
| 2017/0242963 A1* | 8/2017 | Cohen | G06F 19/321 |
| 2017/0286600 A1* | 10/2017 | Hasan | G06F 19/324 |
| 2017/0372096 A1* | 12/2017 | Yousfi | G06F 21/6254 |
| 2018/0137938 A1* | 5/2018 | Vaddiraju | G16H 40/67 |
| 2019/0146165 A1* | 5/2019 | Lee | H01S 5/02252 385/14 |
| 2019/0190897 A1* | 6/2019 | Rosenberg | G16H 50/70 |
| 2019/0303609 A1* | 10/2019 | Riddle | G06F 21/629 |

\* cited by examiner

US 11,017,116 B2

SECURE INTEGRATION OF DIAGNOSTIC DEVICE DATA INTO A WEB-BASED INTERFACE

BACKGROUND

A growing number of individuals, as well as a growing number of companies that employ these individuals, are placing a significant emphasis on knowing about and improving their respective general states of health. Employers, for example, often pay for and encourage individuals to take part in health screenings hosted by the employers as a way to express: (1) care for general workforce and key individuals; and (2) a desire for those individuals to keep informed about their health and seek out methods for improvement to prolong their lives. Advancements in diagnostic devices that measure or test for various biometric parameters have enabled fast and accurate testing that can be readily reported in an electronic form on said electronic devices. These biometric parameters are considered to be baseline indicators of health and/or the presence of major medical conditions, such as height, weight, heart rate, glucose level, and LDL, HDL, and total cholesterol levels.

However, electronic storage of these results in locations that can be accessed by controlled and secure methods (by e.g., individuals, hospitals, insurance companies, employers, and/or government organizations), often involves time consuming and sometimes rigorous data entry on paper or through intermediate devices. All this may occur before the results are loaded, entered, or transmitted to, and stored in a final location (e.g., an enterprise database). This may increase the risk of reporting errors or a breach in privacy of a tested individual. For example, test and identity information can be inadvertently left in a memory of an intermediate device.

Take, for example, the situation of a health screening that an employer hosts for several employees (such as a "wellness exam"). Each individual tested may go to each of several stations with a different biometric parameter being tested or measured at each station. For any individual tested during the health screening, an operator of a diagnostic device may test or measure the individual with the diagnostic device, read the results from the diagnostic device, and transfer the results by hand to a summary sheet the individual carries to each station. Copies of the summary sheet may go the individual, the company employing the individual, and the company administering the test. For either of the companies to have comprehensive records of all results for all individuals, the results of each sheet may have to be separately entered into an electronic database. This is a labor and time intensive process and the chances of data entry errors are very high.

In another example, the operator may enter the results into an intermediate device. The intermediate device may include an electronic personal or enterprise device owned or issued to the operator. The intermediate device can locally store the results before transferring them to a central location, such as a server. In another example, the results may be stored on a portable storage device, such as a USB drive, for transfer at another time. There is a significant risk that any of these devices may be accessed, either through a network or by the intermediate device being lost or stolen, by individuals who are not authorized to know such information, and therefore breech tested individuals' privacy. Further, such storage on unsecure intermediate devices may be in contravention to state and federal privacy protection laws, and thereby expose companies, health care providers, and/or testing facilities to legal liability.

These and other issues are addressed by a system and method for securely integrating information from diagnostic devices, of the present disclosure.

SUMMARY

Examples described herein include systems and methods for securely integrating device data generated by diagnostic devices into a backend database server. The integration can include device data being transferred from a diagnostic device, and processed into data elements that are stored in backend database server. A user device can allow for the transmission without storing the device data or data elements in the user device's memory.

An example method can include a user device being paired to an external device by a native application that is installed on or otherwise managed by the user device. The external device may be attached to, built within, or generally in communication with a diagnostic device. The pairing may be implemented via BLUETOOTH, WIFI, or through a network. In addition, the native application can establish a data channel between itself and the external device.

Before, during, or after the pairing and the establishment of the data channel, the diagnostic device can analyze or measure a specimen (e.g. blood, skin, a person, etc.), generate device data including a value corresponding to a result of the analysis or measurement, and send the device data to the external device. As a result, the external device can send the device data to the native application that can be monitoring for device data.

The native application can receive the device data and establish a secure connection with a backend over a network, such as the internet (e.g. via a website) or a local network. The native application can initiate a data call function of a remote application on the backend along with or after establishing the secure connection. In response to at least the establishment of the secure connection, the backend can communicate with the native application to load the remote application in the native application which implements a user interface of the remote application in a webview component of the native application. In one example, the webview component can be a simplified browser that persists within the native application.

In one example, the native application can load the remote application with an active data call function. The native application can transfer the device data to the remote application in response to the active data call. The device data can be temporarily stored in RAM of the user device but is not accessible by any other application running on the user device.

The remote application may be provided by the backend and include a plurality of pages. Each page may include a respective set of local fields, and each local field may correspond to a biometric parameter, patient identifying information, or diagnostic device identifying information. The data call function can cause the remote application to call for data and receive device data that the remote application can validate while running in the webview component of the native application. Validating the device data can include the remote application processing the device data in order to: (1) determine if any data composed thereof is compatible with the remote application; and (2) further process (e.g. parse, extract from) the device data into data elements that may correspond to local fields of the remote application. The remote application can further process the data elements by associating each to a respective corresponding local field of a page loaded with the interface through the webview component. The validating process may not include permanent storage of any data elements on the user device.

The user interface of the remote application, being implemented through the webview component, may display a result of the validating process through a display of the user device, or at least one control data element identifying a diagnostic device that generated the device data; and request authorization for preliminary integration of the device data. Preliminary integration may include the remote application populating local fields of a current set of local fields (current page) with data elements from the device data. If authorized, the remote application can populate the local fields of the current set with the data elements respectively associated therewith.

Further in response to a preliminary integration being authorized, the remote application operating within the webview component of the native application may display local fields populated with data elements that have been respectively associated with the local fields, a first control data element corresponding to an identity of a patient, and a second control data element corresponding to a diagnostic device. With these aspects displayed, the remote application may request authorization to integrate the device data. If authorized, the remote application may generate an integration instruction that defines: (1) an association between the data elements populating the local fields and the first and second control data elements; (2) the associations between the data elements and the local fields. Further, the remote application can cause the integration instruction and the data elements to be transferred to a backend database server for permanent storage. The backend database server may include groups of storage fields. Each group of storage fields may be associated with a respective first control data element, and include a corresponding storage field for every local, field for all the sets of local fields of the remote application.

In another example, implementation of a user interface of a remote application through a webview component of a native application, can occur before device data is received by the native application. In addition, prior to receipt, the user interface may load a page of the remote application including at least one control data element corresponding to an identity of a patient. Stages in which device data is received and validated by the remote application, without being stored permanently on a user device, may be implemented subsequently; but prior to the remote application requesting authorizations for preliminary integration and integration. In each request, a control data element corresponding to an identity of a patient may be displayed, but only associated with data elements from device data once integration is authorized. Further, the control data element and the data elements from the device data are not permanently stored in a memory or other location of a user device.

The example methods summarized above can be incorporated into a non-transitory, computer-readable medium having instructions that, when executed by a processor associated with a computing device, cause the processor to perform stages for performing secure integration of device data. Additionally, the example methods summarized above can be implemented in a system including, for example, a diagnostic device, an external device, a user device, a backend providing content and database server components, or any combination thereof.

Both the foregoing general description and the following detailed description are exemplary and explanatory only and are not restrictive of the examples, as claimed.

DETAILED DESCRIPTION

Reference will now be made in detail to the present examples, including examples illustrated in the accompanying drawings. Wherever possible, the same reference numbers will be used throughout the drawings to refer to the same or like parts.

Figure 1:
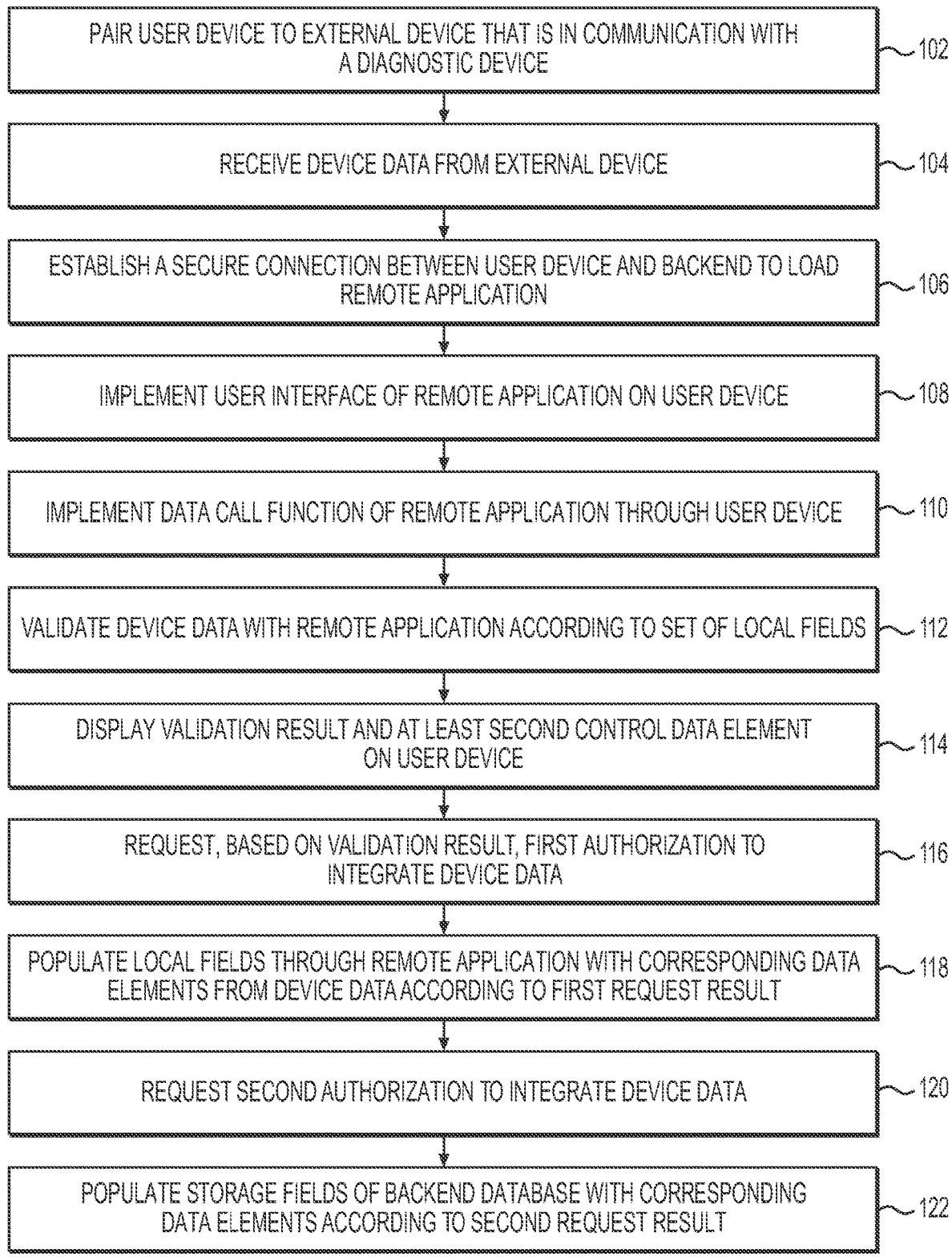
FIG. 1 illustrates an exemplary method executed in a system, according to an aspect of the present disclosure.

FIG. 1 illustrates an exemplary method executed in a system, according to an aspect of the present disclosure. At stage 102 of the method, a user device can pair with an external device directly or over a network according to a communication protocol, and the external device may be connected to or otherwise be in communication with a diagnostic device. The user device can be any computing device, such as a cell phone, laptop, personal computer, or workstation. The user device can include a non-transitory, computer-readable medium containing instructions that are executed by a processor in the user device. Example non-transitory, computer-readable mediums include RAM and ROM, disks, and other memory and storage that is accessible by a USB, a floppy drive, CD-ROM or DVD-ROM drive, and a flash drive, among others. The processor can be any logic processing unit, such as one or more central processing units (CPUs), digital signal processors (DSPs), application specific integrated circuits (ASICs), field programmable gate arrays (FPGAs), and similar devices.

The external device may be a BLUETOOTH or WIFI component (e.g. adapter) that can be attached and removed from the diagnostic device. In another example, a component such as a BLUETOOTH or WIFI adapter may be incorporated in the diagnostic device. According to an aspect of the present disclosure, the external device may utilize one communication protocol (e.g. a direct connection through a circuit) for receiving and sending data to the diagnostic device, and a different communication protocol for communication and data exchange with the user device. According to another aspect of the present disclosure, the external device may utilize the same communication protocol for communication and data exchange with the diagnostic device and the user device.

During enrollment, a management server can receive device information about the enrolling computing device, such as a device model and current firmware version. The device model can indicate a particular make of the computing device. The device model can also indicate the source of the computing device, such as the manufacturer, OEM, carrier, or firmware supplier of a device. In one example, the management server identifies an applicable firmware server for an enrolled device by receiving the device model and linking that to a firmware server in a database.

The diagnostic device can be any device used to test, measure, and/or report any biometric parameter. In one example the diagnostic device may be any device (e.g. a CardioChek® analyzer) configured to analyze metabolic blood chemistry panel test strips (lipid panel test strips), and thereby measure glucose, low-density lipoprotein (LDL) cholesterol, high-density lipoprotein (HDL) cholesterol, total cholesterol, very-low-density lipoprotein (VLDL) cholesterol, and triglycerides. The results of these measurements may be utilized in testing for lipoprotein metabolism and lipid disorders (e.g. diabetes mellitus), atherosclerosis, and renal and liver diseases. In other examples, the diagnostic device that is in communication with the external device can include: an oximeter that measures oxygen saturation; a sphygmomanometer (blood pressure meter) that measures blood pressure; a dedicated glucose meter that determines approximate concentration of glucose in the blood; a scale that measures a person's weight; or a stadiometer that measures a person's height. In still other examples, the diagnostic device may include a thermometer, a heart monitor, a stethoscope, or other device that measures biometric parameters such as temperature, heart rate, and respiration rate.

The pairing process of stage 102 of the method can include a native application that is provided on the user device, connecting the user device to one or more external devices directly or via a network. A connection between the user device and the network can be accessed by the native application; or implementation of the native application can cause the user device to connect to the network. In one example, the network can be any local network that allows devices to communicate with each other without requiring use of the internet. In one example, BLUETOOTH discovery can be used to identify and pair devices based on available BLUETOOTH functionality or components. Further, other forms of near-field communication (NFC) can be used in a similar method to BLUETOOTH. In addition, an open-source protocol such as BONJOUR can be used to perform pairing. Still further, pairing can be performed by ANDROID NEARBY, which can identify devices running an ANDROID operating system. Alternatively, the network can be a WIFI network within a home, workplace, or public space.

Stage 102 may include a sub-stage subsequent to the pairing between the user device and the external device which includes the user device establishing a data channel with the external device. Through the data channel, data from the diagnostic device may be transferred from the diagnostic device to the user device through the external device. It will be understood that the external device, in addition to transferring data from the diagnostic device, may generate and send its own data to the user device. As discussed in further detail with reference to FIGS. 2 and 4, the user device may be paired to more than one external device and implement a process for establishing data channels with certain external devices at certain times based on various criteria.

Stage 104 of the method can include the user device receiving device data from the external device through the native application. The device data may be received by the external device in response to an operation by the diagnostic device.

The device data can include data, a value, and/or sets of data that indicate that the diagnostic device has executed an analysis or taken a measurement, and a result of the analysis, value of the measurement, or representation thereof. The native application can be a managed application or other application installed on the user device. The user device can receive the device data as a result of a monitoring protocol executed by the native application. In another example, the device data may be received as a result of a data transmission initiated entirely by the external device.

At stage 106 of the method, the native application can establish a secure connection with the backend. According to an aspect of the present disclosure, the native application can access the backend over a network, such as the internet (e.g. via a website) or a local network (e.g. an enterprise network). In addition, the secure connection can optionally be established through an authentication process with respect to the user device (e.g. via an authentication token issued for the user device), and/or an operator of the user device (e.g. via a single sign-on ("SSO")). As referred to herein, an operator may be a medical professional such as a doctor, nurse, physician's assistant; a laboratory or hospital technician; or the like.

As part of stage 106, establishment of the secure connection can be followed by the native application calling for, and thereby initiating, a local data call function of a remote application provided by the backend. The communication, which may be implemented through an Application Programming Interface (API) of the native application, can call a function in the remote application that monitors (look/listen for) for data to be processed (parsed, analyzed, compiled, etc.). Thus, the native application can initiate the local data call function of the remote application by communicating with the backend in response to receiving the device data from the external device.

In one example, the native application can receive the device data and then delete it if the secure connection is not established with the backend within a predetermined period of time. In another example, establishing the secure connection may be a condition for checking for or receiving the device data such that stage 104 is preceded by stage 106.

In another example, in addition to the reception of, the monitoring for the device data can be conditioned on the establishment of the secure connection with the remote application. For each of the examples in which providing a secure connection is a condition for checking for or receiving device data, the calling of the local data call function in the remote application may be conditioned on the reception of the device data. The implementations described herein with respect to establishing a secure connection with backend may provide additional assurance that the device data can be transferred to the remote application implemented through the webview component without being permanently stored on the user device.

According to an aspect of the present disclosure, the remote application can load in an internet browser that is being implemented by a device. Under this scheme, the remote application avoids taking up memory or storage on the device implementing the internet browser. In another example, the remote application can be a software as a service ("SaaS") application that runs in a cloud. The backend can be a network of servers, some of which can be located remotely from one another. In another example, the backend can be server can be a single server with multiple purposes. In yet another example, the backend can be a server (or group of servers) dedicated to the operations described herein. In still another example, the backend can be a cloud server.

Stage 108 of the method can include an implementation of a user interface of the remote application on the user device. In one example, the native application may include a webview component that is configured to implement the user interface. In one example, the webview component can be or call a simplified browser that persists within the native application, and is exclusively assigned to loading the remote application. Loading the remote application through the webview component may add an additional layer of protection that prevents device data from the diagnostic device, or data elements extracted from the device data, from being permanently stored on the user device. In one example, the webview component of the native application and implementation thereof, provides selectable backward, forward, refresh, and stop options for navigating and managing the state (e.g. which page is loaded in a user interface) of the remote application.

In one example, the remote application and user interface thereof includes a plurality of pages, and each page can include a respective set of local fields. The local fields may be constituted as part of a data map for a respective page of the remote application. In one example, each page is expressed as a client-side form, and a set of local fields for each page is expressed as a set of data entry fields in a respective client-side form. Any data incorporated into one of the local fields of a page of the remote application may exist only as part of the data map for a page, until a multi-stage authorization process is completed. Accordingly, no data provided in the local fields is stored in or accessed from a storage memory of the user device.

In one example, the authentication process may include the SSO as described herein, and the secure connection is established through a two-part process that includes stage 106 and stage 108. In particular, establishing the secure connection can include a device authentication at stage 106; and at stage 108, the SSO authentication being implemented through the user interface, which has been loaded on the user device by the webview component of the native application.

It will be understood by those of ordinary skill in the art that the native application may access the backend and cause a separate browser application on the user device to load the remote application including the user interface. This may be in addition to, or an alternative capability with respect to the utilization of the webview component as described herein. Using a separate browser implementation may be desirable to reduce the complexity of operations performed by the native application in cases in which, for example, the user and external devices are restricted to use within an enterprise network that manages access to various content on the internet.

At stage 110 of the method, the data call function for the remote application initiated in stage 106 is implemented. The data call function can be provided through a script (e.g. JavaScript) that executes within the remote application. In one example, each page of the remote application may have a respective data call function that can be initiated (called for) by, as an example, the native application.

The native application can facilitate a communication between the remote application and the external device, or cause a call for data from the remote application to otherwise be communicated to the external device, such that the external device can respond to the call for data by transmitting device. In particular, implementation by the native application of the data call function of the remote application, can cause device data to be transmitted from the native application to the remote application. Accordingly, implementation of the local data call function through the native application can cause the remote application to call for, receive, and accept a raw payload (e.g., device data) received by the native application from the external device, and is not stored permanently by the native application or in any other location (e.g. memory, cache) on the user device.

Stage 112 of the method can include validation of the device data by the remote application. In particular, the remote application may process the device data by first determining if the device data includes any data that is compatible with the remote application. Stage 112 can further include extracting data elements from the device data or parsing the device data into data elements, which may represent or correspond to a result(s) or measured value(s) obtained by the diagnostic device.

In one example, the remote application can run a script that processes the individual data elements in order to identify a type of analysis or a measurement that a value of the data element corresponds to. The identified type can be used to determine if the data element can be associated with any one of a set of local fields of a current page being implemented by the remote application. As a result of the parsing of the device data, and determination that at least one data element corresponds to at least one local field of the current set of local fields, the remote application can associate each of the data elements with their respective corresponding local data fields in the current set. Content, associations, and other definitions of a current page including a current set of local fields can be provided by the backend which loads the remote application in the webview of the native application.

Device data or any data element thereof is not permanently stored on the user device as a result of the device data: (1) passing through the native application for transfer to the remote application; and (2) being processed by the remote application as part of the validation process. Accordingly, any medical data specific to a patient that may be considered highly sensitive and subject to state and federal regulations for protecting the privacy of an individual, is not permanently stored on the user device. At most, the user device provides a view (via the webview component) of the contents of a container (remote application or client-side server), that is wholly separate from, and exists outside of, the user device. The device data can be temporarily stored in RAM on the user device during a transaction before being permanently stored in a database component of the backend. The device data can be deleted from the user device as soon as the transaction is complete. During the transaction the device data is not accessible by other applications or means on the user device. Thus, the device data only exists in RAM for the shortest possible duration while the transaction is taking place.

Further, an identity of a patient, as may be represented by a first control data element described in further detail below, is not stored on the user device, or accessed by the native application or user device with respect to device data. Accordingly, even if the device data was somehow stored on the user device, it would not be stored, or be defined as being associated, with a data element corresponding to an identity of a patient.

At stage 114, the method can include the remote application generating a prompt that is implemented by through the webview component to be displayed on a display of the user device. The remote application can generate the content of the prompt based on a validation result of stage 112. According to an aspect of the present disclosure, the prompt generated by the remote application can indicate: (1) whether or not the device data is compatible with the remote application, (2) whether there is at least one data element of the device data, excluding the first or a second control data element that may or may not be included in the device data, that corresponds to at least one local field of a current page (i.e. current set of local fields); and (3) at a minimum, a value of the second control data element, which can correspond to a diagnostic device that generated device data that was validated in stage 112. In another example, the prompt may include the first control data element. Accordingly, the prompt generated in stage 114 may provide an operator of the user device, which may likely be the same as the operator of the diagnostic device, an opportunity to verify that the device data that has been validated in stage 112, was generated by the diagnostic device the operator expected it to come from (and, in one example, is for the patient the operator expects).

In one example, the first control data element can correspond to an identity of a patient being analyzed or measured by a diagnostic device from which a current device data was generated. Further, the second control data element can correspond to at least one of a type (e.g. model, measured/analyzed biometric) and a unique identifier (e.g. serial number) of the diagnostic device from which the current device data was generated. In another example, a third control data element may be displayed in the prompt and correspond to a lot number of a test strip, and may be displayed with the second control data element.

In one example in which the validation result indicates the device data is compatible with the remote application, and there is a corresponding non-control data element, the remote application can progress to generating a request in stage 116. In another example where the validation result indicates a different result than previously described, the remote application can generate a prompt in the form of a notification indicating the device data is not compatible with the remote application or cannot be accepted by a current page (i.e. current set of local fields). Such may be the case where the remote application validates device data with a set of local fields that correspond to biometric parameters that are not analyzed and/or measured or are different from a current group of biometric parameters analyzed and/or measured, by a current diagnostic device that generated the device data. In either case the method may end. However, in one example of the present disclosure the remote application can include a page with a set of local fields that does correspond to data elements of a current device data, and can be accessed.

The method at stage 116 can include the remote application generating a prompt that is implemented by the native application through the webview component, and requests authorization for a preliminary integration of device data. Preliminary integration may encompass local fields of a current page of the remote application (i.e. the current set of local fields) being populated with data elements of the device data according to associations determined between the data elements and the current set of local fields in stage 112.

In one example, input from an operator in response to the prompt can be recognized by the remote application as a first request result and indicate that preliminary integration has been selected. As a result, the method can progress to stage 118 as described herein. Alternatively, the operator can make a selection indicating preliminary integration has been declined such that in one example, the remote application or the backend server can delete the device data, and the method ends. In another example, the method can continue where preliminary integration is not selected, and a series of different prompts requesting an operator select a different page can be generated by the remote application.

At stage 118 of the method, the remote application can populate a current set of local fields (i.e. a set of local fields associated with a current page of the remote application) according to the first request result of the authorization request generated in stage 116. More specifically, in one example, device data can be validated in stage 112; the user device can display a positive validation result in stage 114; a prompt can subsequently be generated by the remote application and responded to by an operator in stage 116 such that a first request result indicates that a preliminary integration has been selected; and a current set of local fields can be populated in stage 118 with data elements from device data according to the associations determined in stage 112.

In one example, the method at stage 118 can include a current set of local fields being populated in the remote application according to the associations determined in stage 112. In one example, the populated local fields can be accessed by the remote application for display on the user device. Further, the control data elements may only be associated with a validation result until a second authorization process is performed. Accordingly, the combination of control data elements and data elements of populated local fields may only exist on a backend as described herein.

The remote application can generate one set of pages, each page including a respective set of local fields. The remote application can temporarily associate the set of pages with a combination of one or more control data elements; populate the local fields of a page with data elements based on determined associations; and clear or delete the local fields following a subsequent stage of the method. The remote application, as implemented through the webview component of the native application, can provide a library of pages (sets of local fields) that are selectively loaded and modified (added to) only within the remote application.

In any of the examples described herein with respect to stage 118, private and potentially sensitive medical data is not permanently stored on the user device, and may in some examples, not even be associated with an identity of a patient in a memory of the user device in a manner that can be later referenced. Rather, the device data can be temporarily stored in RAM of the user device and is not accessible by any other application.

The method at stage 120 can include the remote application generating a prompt that requests authorization for an integration of device data. Prior to, or concurrent with the generation of the prompt, the remote application may provide a representation of the populated fields that may have resulted in stage 118. Thus, a current page of the remote application may be displayed on the user device with at least one local field of a respective set populated with a corresponding data element. In addition, along with the request for authorization and the populated local field(s), the first and second control data elements can be displayed.

An advantage of the present disclosure includes an operator being able to view medical test data (data elements of device data) from a test performed by the operator or another individual with a diagnostic device, without having to manually record the test results in a written or electronic format. Further, the test data may only exist a form separate from a control data element corresponding to an identity of a patient until an operator authorizes an association therebetween. Thus, an operator can see if test data in the form of data elements populating local fields of page is correct, and has been designated for association with the correct patient, before the data elements are permanently stored in any location.

In one example, input from an operator in response to the prompt can be recognized by the remote application as a second request result, and indicate that integration has been selected. As a result, the method can progress to stage 122 as described herein. Alternatively, the operator can make a selection indicating integration has been declined such that in one example, the remote application clears any populated local field, deletes the device data from the user device, and the method ends. In another example, the method can continue where integration is not selected and a series of different prompts can be generated by the remote application allowing an operator of the user device to change a first control data element input or put integration on hold.

At stage 122 of the method, the remote application and/or the backend server can transfer data elements to a backend database server for integration based on the second request result. In contrast to preliminary integration, integration can include a database component of the backend permanently storing data elements of device data in storage fields. The storage fields can: (1) correspond to respective local fields of the remote application; and (2) be permanently associated with a control data element such as the first control data element. Thus, the backend database server can include, or be capable of generating, a set, or a set of sets, of storage fields that are permanently associated with a single first control data element (e.g. a particular patient).

In one example, data elements can be modified or updated to include a definition or identifier of an association, which identifies a local field (via definition of a parameter of a respective identifier thereof) the data element corresponds to and was associated with by the remote application implemented in the webview component. This definition or identifier for the data element can be recognized by the backend database server for determining which storage field a data element will populate and ultimately be stored in or stored as being associated therewith. The storage fields may only be populated once the authorization processes of stages 114 and 120 are completed. Further, any data element with which a storage field is populated, does not get permanently stored on a user device. Stage 122 of the method can also include the remote application 300 clearing the data elements from the current set of local fields, and deleting the device data and data elements from the remote application and the user device.

Advantages of the present disclosure include the transfer, display, review, and approval of test data via a user device that is separate from a diagnostic device that performed a test or measurement, without: (1) the inconvenience of having to manually enter the test data, thus increasing speed and minimizing the occasion for reporting errors; or (2) permanently storing the test data on the user device so that any test data and/or identify information about the patient is at risk of being stored on a device that is not continuously monitored by or connected to a network that protects the security of sensitive information such as patient medical records. Further, with the capability provided by the native application to establish data channels with more than one diagnostic device, the method of FIG. 1 can be performed simply and quickly with multiple diagnostic devices that have been used to test or measure some biometric parameter of a patient. Further, the interaction between the native application and remote application, in conjunction with a patient selection method through the remote application that is controlled by an operator, allows an operator to use the same diagnostic device on different patients in succession while insuring that medical test is recorded with respect to the correct medical patient.

Figure 2:
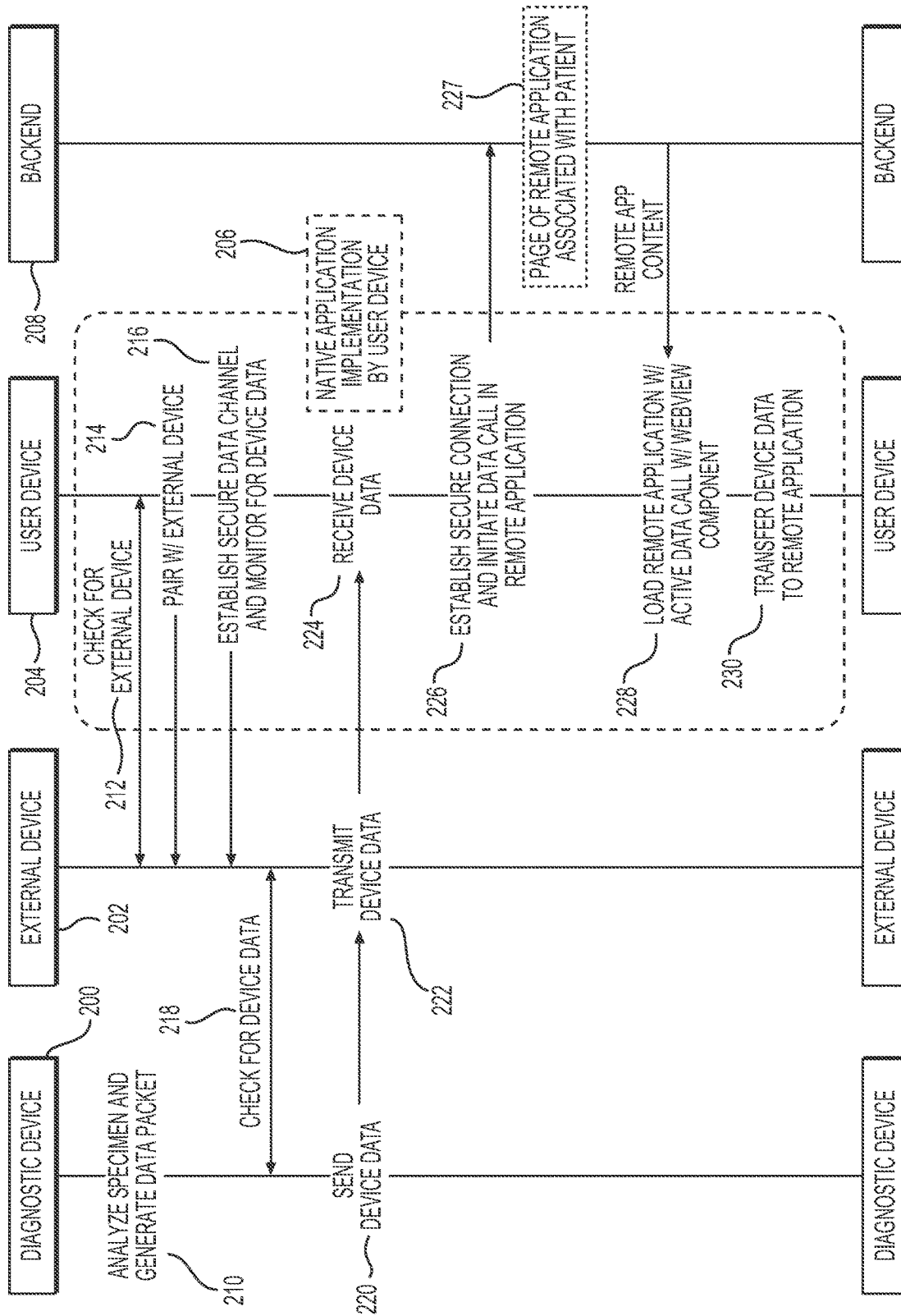
FIGS. 2 and 3 illustrate exemplary methods executed in a system, according to an aspect of the present disclosure.
Figure 3:
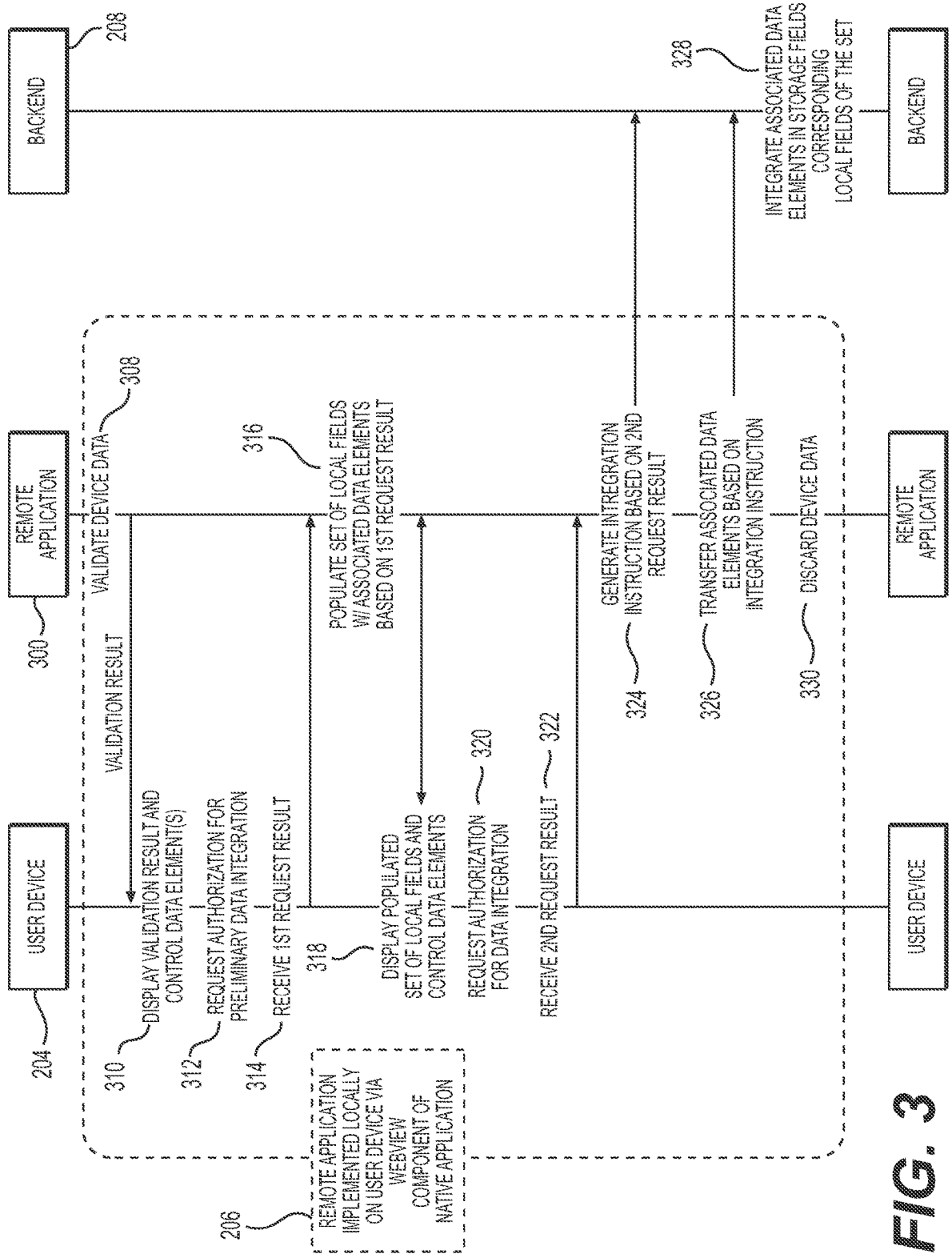

FIGS. 2 and 3 illustrate exemplary methods executed in a system, according to an aspect of the present disclosure. In particular, FIG. 2 illustrates a method in which device data: can be generated by a diagnostic device 200; transferred, through a user device 204 via a native application 206, from an external device 202 to a remote application 300; and not be persistently stored in a memory of the user device 204.

At stage 210 of the method, the diagnostic device 210 can analyze a specimen and generate device data. The specimen may be a biological specimen extracted by the diagnostic device 200 directly from a patient, or a container or other vessel (e.g. a test strip) that contains or is embedded with a specimen from a patient. In another example, a patient, or part thereof, constitutes a specimen and the external device 200 analyzes the specimen in the form of a measurement of a biometric parameter (e.g. height, weight, respiration rate, heart rate, etc.) exhibited by the specimen.

At stage 212 of the method, the native application 206 of the user device 204 can attempt to discover external devices 202 for the purposes of pairing with any discovered external devices 202. The discovery process can include the native application 206 identifying other devices, via BLUETOOTH, or through a network such as a WIFI network or a local network, that enables devices to communicate with one another without requiring the use of the internet. The given external device 202 may be connected to or built within the diagnostic device 200 as described herein with reference to FIG. 1. The external device 202 can primarily function as a communication bridge between the diagnostic device 200 and the user device 204.

Once the user device 204 has discovered the external device 202 in stage 212, the user device 204 executes a pairing process in stage 214. The pairing process can be facilitated by the native application 206 of the user device 204 as described herein with regards to stage 102 of FIG. 1.

Stage 216 of the method can include the native application 206 establishing a data channel with the external device(s) 202. The data channel enables the user device 204 to exchange data with the external device 202. In one example, the user device 204 may be capable of pairing to an unlimited or first number of devices; but may limit or only be capable of having a second number of data channels established with external or other devices. The limit or second number being less than the first number. The native application 206 can therefore manage which devices can exchange data with the user device 204 by selectively establishing data channels only with those devices that are part of, connected to, or associated with diagnostic devices 202. The native application 206 can further regulate the number of and/or which diagnostic devices 200 have data channels based on a level of activity of the diagnostic devices as indicated by respective external devices 204. In one example, the native application 206 can establish a respective priority on the user device 204 above other applications and/or functional aspects of the user device 204, in order to manage which devices the user device 204 has a data channel established therewith.

At stage 218 of the method, the external device 202 can scan or otherwise communicate with the external device 200 to determine the existence of device data. The diagnostic device 200 can send the external device 202 device data in response to the external device 202 checking for device data. In another example, stage 218 may be obviated by a function of the diagnostic device 200 in which the device data, once generated by the diagnostic device 200, is automatically sent to the external device 202 at stage 220 where a connection between the devices has already been established.

According to an aspect of the present disclosure, the device data may be any combination of informational data capable of being transferred electronically or wirelessly from one device to another device. In one example the external device 202 can be an adapter (e.g. a BLUETOOTH dongle, WIFI USB) or other removable input/output device, that is operational upon connection with an external port of the diagnostic device 200. In another example, an input/output port of the diagnostic device 200 may be a printer port (for example with a CardioChek® analyzer), and the device data can include a series of print commands interspersed with test or analytical data from a testing or measuring process performed by the diagnostic device 200. The diagnostic device 200 can cause a flag to be read by the external device 202 or send the external device 202 a signal or message to indicate that device data has been generated.

Stage 222 of the method can include the external device 222 sending the device data to the user device 204 in response to receiving the device data from the diagnostic device 200. In another example, the device data can be sent on a conditional basis as described herein. One of ordinary skill in the art will understand that the series of stages including stages 212, 214, and 216, may be implemented concurrently with the series of stages including stages 210, 218, 220, and 222.

At stage 224 of the method, the native application 206 of the user device 204 can receive the device data. The native application 206, once implemented, may continually receive device data once at least one data channel is established with a given external device 202. As a result, the external device 202 can send the device data at stage 222 over a respective data channel, and the native application 206 can receive the device data 224. In one example, stage 224 may be automatically implemented once the device data is generated by the diagnostic device 200.

In yet another example, the native application 206 conditioning a check for device data at stage 216, or the receiving of an export instruction in stage 224, on the establishment of a secure connection between the user device 204 and the backend 208. Such a secure connection may be established through the native application 206, as described herein with reference to stage 226.

Stage 226 of the method can include a first and a second sub-stage. The first sub-stage can include the native application 206 establishing a secure connection with the backend 208. The native application 206 can access the backend 208 over a network, such as the internet (e.g. via a website) or a local network (e.g. an enterprise network). In addition, the secure connection can optionally be established through an authentication process with respect to the user device 204 (e.g. via an authentication token issued for the user device 204), and/or an operator of the user device 204 (e.g. via a single sign-on ("SSO")) as described herein with reference to stage 106 of FIG. 1.

In addition to establishing a secure connection, in the second sub-stage of stage 226, the native application 206 can call for, and thereby initiate, a data call function of a remote application provided on the backend 208. In one example, the local data call function may be initiated automatically upon the establishment of the secure connection between the native application 206 and the backend 208. In another example, where checking for or receiving device data by the native application 206 is conditioned on the establishment of a secure connection, the native application 206 may initiate the data call function in the remote application after device data is received (which occurs subsequent to the establishment of the secure connection). The remote application can be a web application and the backend can function as web server that supplies remote application content to the native application 206.

In one example, each page of the remote application can have a respective data call function. The device data may include a device type that the native application 206 can recognize. Further, the native application 206 may define which data call function to initiate in the remote application based on a device type, a data type of device data, or other information in the device data. Accordingly, the native application 206 may selectively initiate a data call function for a specific page of the remote application.

The method of FIG. 2 may optionally include stage 227 in which the backend 208 can assign a page of the remote application to be loaded in stage 228 to a patient. In one example, the patient may be represented by a first data control element that may include the patient's name, an identifier assigned to the patient, or another representation of identifying information specific to the patient. The backend 208 may associate the patient (first control data element) to a page that is to be loaded (with/as an interface of the remote application) on the user device 204 through the native application 206. This can be based on operator input elicited through a series of prompts or selection options; through a registration process which the backend 208 implements through user device 204 or another device; or registration information accessed from a network based on recognized communication protocols, recognized stages of a registration process with respect to when test data is obtained, location analysis, or other decision criteria. In one example, the backend 208 can independently, or through operator input, search a network or other information source for a patient schedule or a last patient checked-in or registered to associate to a page to be loaded.

At stage 228 of the method, the native application 206 can communicate with the backend 208 and load backend-supplied content for a user interface of the remote application on the user device 204. In one example, the native application 206 may include a webview component configured to implement the user interface as described herein with reference to stage 108 of FIG. 1. As such, the webview component can be or call a simplified browser that persists within the native application 206, and is exclusively assigned to loading the remote application. The webview component of the native application 206 may provide selectable backward, forward, refresh, and stop options for navigating and managing pages and/or a general state of the remote application.

Stage 228 of the method further includes loading the remote application with an active data call function as a result of being initiated in stage 226 by the native application 206. As described herein with reference to stage 110 of FIG. 1, a data call function can be local to the remote application such that a script (e.g. JavaScript) that performs the function (call) only exists within the remote application. Implementation of the data call function can cause the remote application, being implemented in the webview component, to call for and receive data. In one example, the data call function can be specific to a page of the remote application, and therefore define the type of data the remote application expects to receive.

At stage 230 of the method the native application 206 can send the device data to the remote application. Thus, implementation of the data call function can cause the remote application to call for, receive, and accept a raw payload (device data) generated by the diagnostic device 200, such that the payload passes through the native application 206 in stage 230 and is not permanently stored on the user device 204. Rather, the device data is temporarily stored in the user device 204 and is not accessible by other applications other than the remote application via the native application 206. In one example the raw payload may be modified by the external device 202 depending on a respective communication protocol.

According to an aspect of the present disclosure, a modification of the method of FIG. 2 may include implementing a sequence of stages, including the first sub-stage of stage 226, optional stage 227, and stage 228, independently of and before any of stages 210 through 224. Accordingly, either by operator use of the user device 204 or some other initiating act occurring before the user device 204 is paired to or receives an export instruction from the external device 202, the modified method of FIG. 2 may provide for: the native application 206 establishing a secure connection with the backend 208 (and thus call the application); a patient (first data control element) being associated with a page of the remote application that is to be loaded; and the remote application, including the associated page, being loaded on the user device 204 with the webview component of the native application 206.

FIG. 3 illustrates a method in which the user device 204 can: operate through the native application 206 to implement a remote application 300, the content of which is supplied by the backend 208; and obtain authorization from an operator to integrate data elements from validated device data into storage fields of a database component of the backend 208.

The local fields of the remote application 300, which may be content supplied by the backend 208, include data entry fields, each associated with a particular category or identifier that corresponds to information that can be used to describe or identify a patient, operator, or a biometric parameter including a physical or biological measurement, test, or test analysis. The remote application 300 may maintain a list of local fields, a definition for each, and a definition for a type of data that can be accepted as corresponding to each field. In one example, the remote application 300 may provide a library of local fields organized in sets, each set being expressed in the form of a page in the user interface of the remote application 300. Each page then includes each local field of the respective set.

In one example, the remote application 300 may maintain a limited number of groups of sets of local fields, each group comprising an entirety or a portion of the library. Each group may be temporarily associated with each patient (represented with a respective first data control element) of a limited number of patients, as assigned on the backend 208, such that test and measurement data can be temporarily stored in corresponding local fields of a group associated with a respective patient (first data control element).

Local fields can correspond to storage fields of the database of the backend 208. The backend 208 can maintain a library of storage fields. In addition, for each patient having a record in the database, a group of storage fields may be maintained, and each group may include a portion or an entirety of the library of the storage fields. Each group is associated permanently to a patient and therefore may define a patient record. Like the local fields, the storage fields include data entry fields, each associated with a particular category or identifier that corresponds to information that can be used to describe or identify a patient, operator, or a biometric parameter including a physical or biological measurement, test, or test analysis. Each local field maintained by the remote application 300 corresponds to one storage field in the library maintained in the database by the backend 208.

At stage 308 of the method, the remote application 300, being implemented in the webview component of the native application 206, can run a script to validate the device data in a manner similar to stage 112 of FIG. 1. In particular, the remote application 300 may process the device data by first determining if the device data includes any data that is compatible with the remote application 300. In one example, the remote application 300 can compare the data elements with the definition and data type for every local field of every set that the remote application includes. The remote application 300 can then extract data elements from the device data or parse the device data into data elements, which may correspond to a result(s) or measured value(s) obtained by the diagnostic device 200. In one example, the remote application 300 can run a script that processes the individual data elements in order to identify a type of analysis or a measurement that a value of the data element corresponds to. The identified type can be used to determine if the data element can be associated with any one of a set of local fields of a current page of the remote application 300.

Stage 310 of the method can include the user device 204, through the webview component of the native application 206, displaying a validation result obtained by the remote application 300 as described with reference to stage 114 in FIG. 1. In one example, display of the validation result, irrespective of the compatibility of the device data or whether a data element corresponds to a local field of the current sent, can be accompanied by a display of a first data control element and a second data control element. In another example of the present disclosure, the validation result can be displayed only along with the second control data element corresponding to an ID or type of the diagnostic device 200.

As discussed herein, the first data control element may include a name, ID number, or other identifier that corresponds to a patient. In one example, the first data control element may be obtained via the user device 204. The remote application 300 may be initiated through the user device 204 or other device prior to any of the stages discussed herein with reference to the methods of FIG. 1, 2, or 3, for the purposes of registering a patient or obtaining registration information about the patient. In one example, after calling the remote application 300 on the user device 204, an operator may be prompted, through the native application 206, to input information about a patient. Alternatively, the remote application 300 may be called where a user device 204, independent of any testing or measuring process, obtains patient identification information as a result of scanning a bar code or identifier, or communicating with an external device that is issued to the patient and is associated with or stores information for that patient.

In one example, the operator may input the patient information which then resides on the remote application 300, but is deleted if testing or measuring data is not obtained within a period of time. In another example, the remote application 300, may communicate with the backend 208 after obtaining patient information through: (1) the user device 204; and (2) an operator, identifier, or issued device. The backend 208 can create a new record, or update a current record for a patient being examined, with only the patient information. In such an example, the remote application 300 may communicate with the backend 208 before the validation result is displayed in stage 310, and the backend 208 can provide the remote application 300 with a first control data element of the most-recent patient information obtained through the user device 204 for a single patient.

Prior to display with the validation result, the first data control element can be associated with the validation result without being associated with the device data or data elements therefrom. Accordingly, the first data control element can remain unincorporated with any potentially private information until appropriate authorization for such incorporation is obtained. In another example, the remote application can associate the first data control element with the device data or the data elements in stage 310.

According to another aspect of the present disclosure, the second control data element can correspond to a device ID, a device type, or a device ID that also expresses a type of the diagnostic device 200. The second control data element may be included as a data element in the device data obtained from the diagnostic device 200. In one example, the remote application 300 can extract the second control data element from the device data and display the second control data element with the first control data element and the validation result in stage 310.

In one example, the remote application 300 can identify a data element from the device data as a potential second control data element and communicate with the backend 208. The backend 208 can maintain a list of device IDs and/or device types which correspond to diagnostic devices that test or measure for data that corresponds to storage fields in the library of storage fields maintained by the backend 208. The backend 208 can communicate with the remote application 300 that the potential second data element corresponds to a device ID or type in the library, and in one example, the remote application 300 can use this information in stage 308 to determine if the device data is compatible with the remote application 300.

At stage 312 of the method, the remote application 300 can use the user device 204, through the webview component of the native application 206, to request authorization for preliminary integration as described with reference to stage 116 in FIG. 1.

At stage 314 of the method, the user device 204 can receive a 1st request result from an operator of the user device 204. As will be understood by those having ordinary skill in the art, the user device 204 may include any computing device that is provided with a display and can receive direct input from an operator. In one example, the user device 204 is a tablet or other mobile device including a touch screen that can display information and receive input from an operator touching particular areas of the display that correspond to selectable options.

Stage 316 of the method can include the remote application 300 populating local fields of a current set of local fields with data elements from the device data that correspond to those local fields. In addition, the remote application 300 can associate the first data control element with the data elements and/or the populated local fields. Accordingly, stage 316 can be the first time that information associated with an identity of a patient is associated with or included as part of the data elements which correspond to the results of the test or measurement completed by the diagnostic device 200.

At Stage 318 of the method, through the webview component, the native application 206 can display the local fields as provided by the remote application 300 and at least the first control data element. Thus, an operator of the user device 204 will have an opportunity to see the values of the results or measurements obtained by the diagnostic device 200; what parameters the values have been associated with (i.e. local field corresponding to a given value); and the identity/identifier of the patient that is being associated with the results and set of local fields being displayed. In addition, for association with the displayed populated fields, the remote application 300 can have an option to accept comments, or to select one of a plurality of values (e.g. a drop box) associated with a diagnosis, state of the patient, and/or impression of the operator (e.g. medical practitioner), which is implemented through the webview component of the native application 206.

Stage 320 of the method can include the remote application 300 generating a prompt that is implemented through the webview component, and requests authorization for an integration of device data as described with reference to stage 120 of FIG. 1. In one example, the prompt for the second request for authorization may be in the form of an option that is always being displayed, but only becomes active as a selectable option once the local fields of the page are populated. In another example, the prompt may be a pop-up window that is placed in front of the populated fields and provides an option to be minimized so that an operator can provide some variable input in, for example, a comment field on the page of the remote application 300.

At stage 322 of the method, the user device 204 can receive a 2nd request result from an operator of the user device 204 in a similar manner to a receipt of the 1st request result in stage 314.

Stage 324 of the method can include the remote application 300 processing the 2nd request result and generating an integration instruction. In one example, the 2nd request result may indicate that the data elements from the device data, as associated to the local fields, are to be stored in a permanent record for the patient being examined or tested. As a result, the remote application 300 can send the integration instruction to the backend 208. Further, the integration instruction can include the first and second control data elements. In one example, the remote application 300 may transfer the data elements to the backend 208 along with the integration instruction, which may include the associations with the local fields, and can be processed by the backend 208. Once accepted by the backend 208, the remote application 300 may discard the device data and data elements from a temporary memory thereof.

In yet another example, the 2nd request result may indicate the data elements are not to be stored. In which case the device data and data elements are discarded by the remote application 300 at stage 324.

In yet another example, the 2nd request result may indicate that an operator wishes to go to (and populate) another page (set of fields) in the remote application 300. As a result, the remote application 300 can maintain the data elements until the earlier of a final integration command is initiated, or a predetermined period of time expires.

At stage 328 of the method, the backend 208 can store the transferred data elements in storage fields that are part of a group of storage fields previously associated with, or newly generated to be associated with, the first control data element that has been associated with the data elements and/or identified in the integration instruction as associated with the transferred data elements. The storage fields in which the data elements are stored, correspond to the local fields of the current set (or sets) of local fields respectively associated with the data elements.

At stage 330 of the method, the data elements and device data are cleared from remote application 300 and deleted from the user device 204. Thus, the device data nor the data elements are permanently stored on the user device 204. In one example, if the user device 204 is turned off or goes into a sleep mode while any stage in the method of FIGS. 2 and 3 is performed, the device data and any data elements extracted therefrom, will be irreversibly erased from the user device. In another example, if the native application 206 or the remote application stops for any reason during the methods, the device data will be wiped from the user device 204, and thus be irretrievable. Accordingly, the methods of the present disclosure ensure that the device data, which may include patient specific sensitive information, is not accessible by applications other than the native and remote applications, does not persist on the user device 204 if it or either of the native and remote applications stops or is put in a sleep mode, and is not permanently stored on the user device 204.

Figure 4:
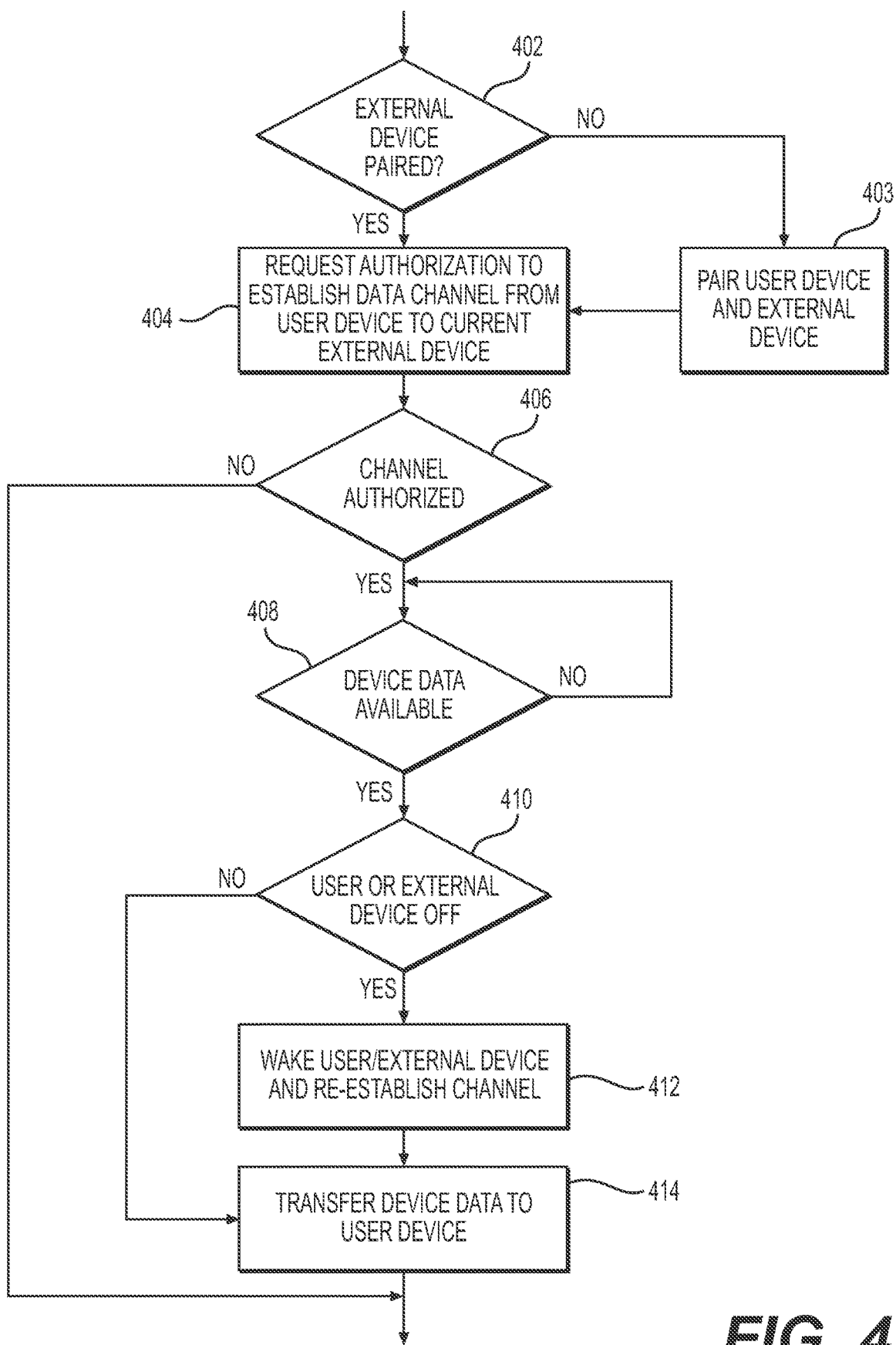
FIG. 4 illustrates an exemplary method of establishing a data channel, according to an aspect of the present disclosure.

FIG. 4 illustrates an exemplary method of establishing a data channel, according to an aspect of the present disclosure. At stage 402 of the method, the user device 204 can determine if it is paired to more than one external device. In particular, the native application 206 can determine the user device 204 is not paired with an external device in stage 402, and in stage 403, find an external device 202 and pair it with the user device 204. Otherwise, the native application 206 can cause the user device 204 to display a prompt that requests authorization to establish a data channel with a current external device 202 in stage 404. In one example, the user device 204 may display a list of paired devices and/or a list of devices for which a respective data channel has been established with the user device 204.

In stage 406 of the method, authorization for establishing the data channel can be denied by an operator, or a timeout for responding to the prompt generated in stage 404 can occur. As a result, the method can end without a data channel being established. Otherwise, the native application 206 will establish a data channel with the external device 202 and determine if device data is available in stage 408. It will be understood that the user device 204 can be paired with multiple external devices 202, and simultaneously have a data channel established with all or some of the external devices 202 it is paired with.

At stage 410, the method can include checking to see if the user device 204 or the external device has been shut off or placed in a sleep mode. In the event this criterion is met, the method can include waking or turning on the user device 204 or the external device 202, and re-establishing the data channel in stage 412. Once the channel is re-established, or if neither of the user device 204 nor the external device 202 was in a sleep mode or turned off, the external device 202 can transmit, and the native application 206 can receive, the device data in stage 414.

The method of FIG. 4 is exemplary of an advantage of the present disclosure directed toward a single user device having data channels established through the native application 206 with multiple external devices, and by extension with multiple diagnostic devices. As with all of the methods described herein, an operator can manage and expedite a series of processes that involve testing a patient with multiple diagnostic devices and recording the results, testing multiple patients with a single or select few diagnostic devices alternated therebetween, or both.

In one example that may correspond to the modified version of the method of FIG. 2, an operator may operate a user device to implement the remote application 300 and access a page for a first patient. The operator can then use a first diagnostic device to, for example, analyze a test strip having a blood sample from the first patient. While the first diagnostic device is subsequently being cleaned, the user device 204 may be operated to populate local fields of the page associated with the first patient, and authorize storage of the populating data elements through the remote application 300. Once complete, but potentially still during a process of cleaning the first diagnostic device, the operator can implement the remote application 300 through the user device 204 and access a page associated with a second patient. The operator can use a second diagnostic device to analyze a blood sample from the second patient, and then have the page for the second patient populated and eventually stored in the database of the backend 208. These processes may be implemented while the first diagnostic device is being cleaned, after which it can be used for a third patient while the second diagnostic device is cleaned.

Further, the authorization processes incorporated in the methods of FIG. 1 (stages 116 and 120), and FIG. 3 (stages 310-322), ensure that cross population of patient records is avoided.

Figure 5:
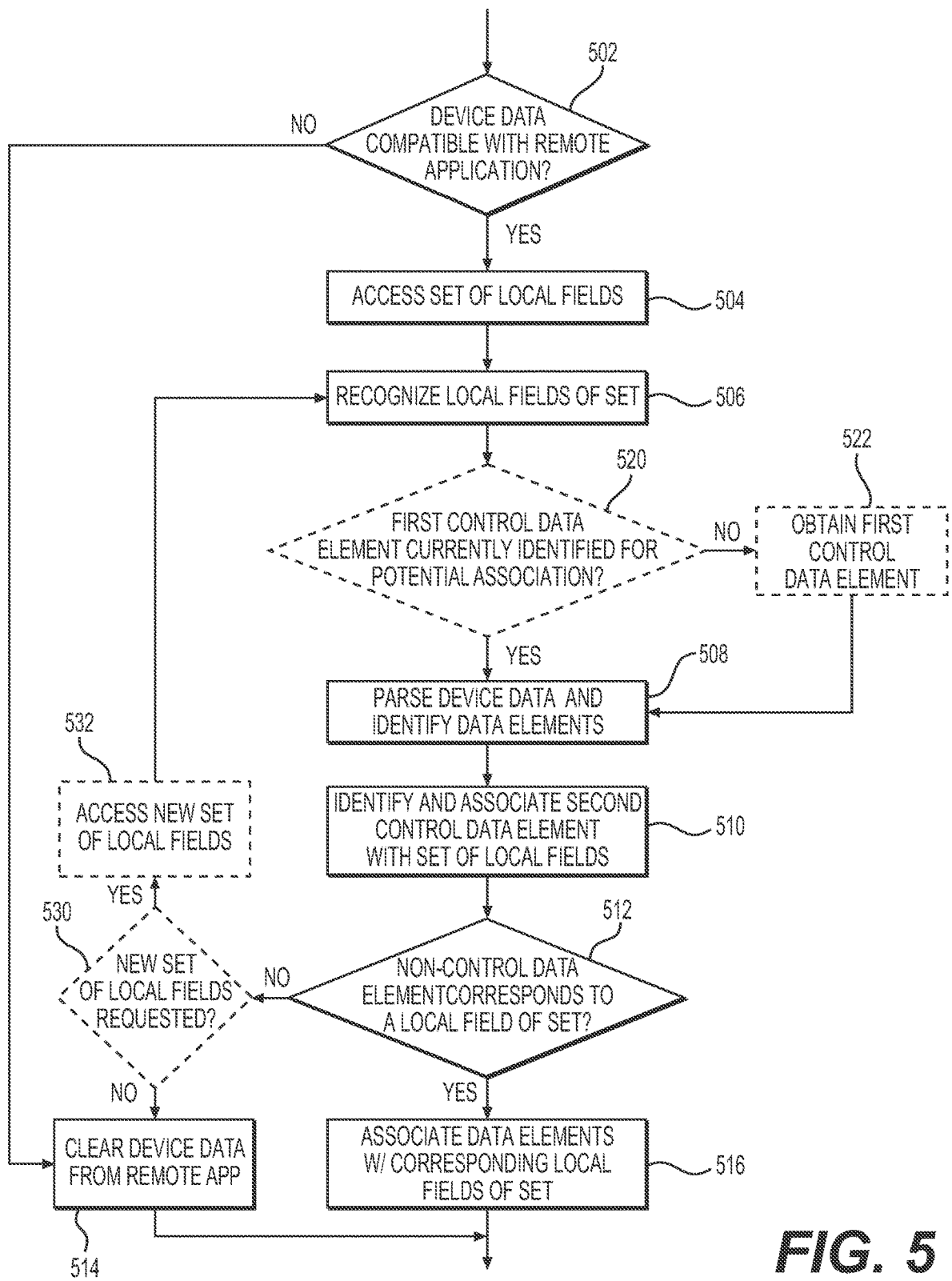
FIG. 5 illustrates an exemplary method of associating local fields with data elements, according to an aspect of the present disclosure.

FIG. 5 illustrates an exemplary method for associating local fields with data elements, according to an aspect of the present disclosure. The method illustrated in FIG. 5 can be part of a validating process of stage 112 of FIG. 1 or stage 308 of FIG. 3. Stage 502 of the method can include the remote application 300, being implemented on the user device 204 through the webview component, determining if device data is compatible with the remote application 300 based on various criteria described herein. Where the device data is not compatible, the remote application 300 discards the device data in stage 514. Otherwise, the remote application 300 accesses a set of local fields. The set of local fields may correspond to a set of fields that are included in a particular page of the remote application 300. Thus, the remote application 300 may include multiple pages, each page having a different set of local fields. In stage 506 of the method, the remote application 300 can recognize the local fields of the set for the purposes of comparing each local field to each data element that is parsed and extracted from device data by the remote application in stage 508.

The remote application 300 can perform the parsing of device data immediately after stage 506, or can optionally check to see if a first control data element is available to be associated with a current page, and potentially the data elements, in stage 520. This may include the remote application 300 communicating with the backend 208 to determine if there is patient information, if any has been obtained through the user device 204 (e.g. via data input, bar code scanning, communication with device issued to patient), that corresponds to a pre-existing patient record in the backend 208. In one example, where a first control data element is not available, one can be obtained through the remote application 300 in stage 522. Where patient information has been gathered but there is not a corresponding record in the database of the backend 208, the first control data element can be determined and a record created. In another example, the remote application 300 can prompt an operator to input the first control data element directly or through a scanning of a bar code or reading of a device issued to the patient. It will be understood that the combination of stages 520 and 522 can be carried out before any of stages 508, 510, 512, or 516.

Stage 510 of the method can include the remote application 300 identifying a second control data element from the device data. In one example, stage 510 can be combined with stage 502.

At stage 512 of the method, the remote application 300 if any of the non-control data elements correspond to at least one local field of a current set of local fields. Where at least one of the data elements corresponds to a local field, all of any additional corresponding data elements (if there be any) are associated with: (1) their respective local fields; and (2) first and second control data elements (if previously obtained). Otherwise, the remote application 300 can delete the device data (including any extracted data elements) in stage 514 of the method.

According to another aspect of the present disclosure, the remote application 300 can optionally prompt an operator to select a new set of local fields in stage 530 where no correspondence is determined in stage 512. Depending on a response from an operator, the remote application 300 can access a new set of local fields in stage 532, or clear the device data in stage 514 of the method.

Figure 6:
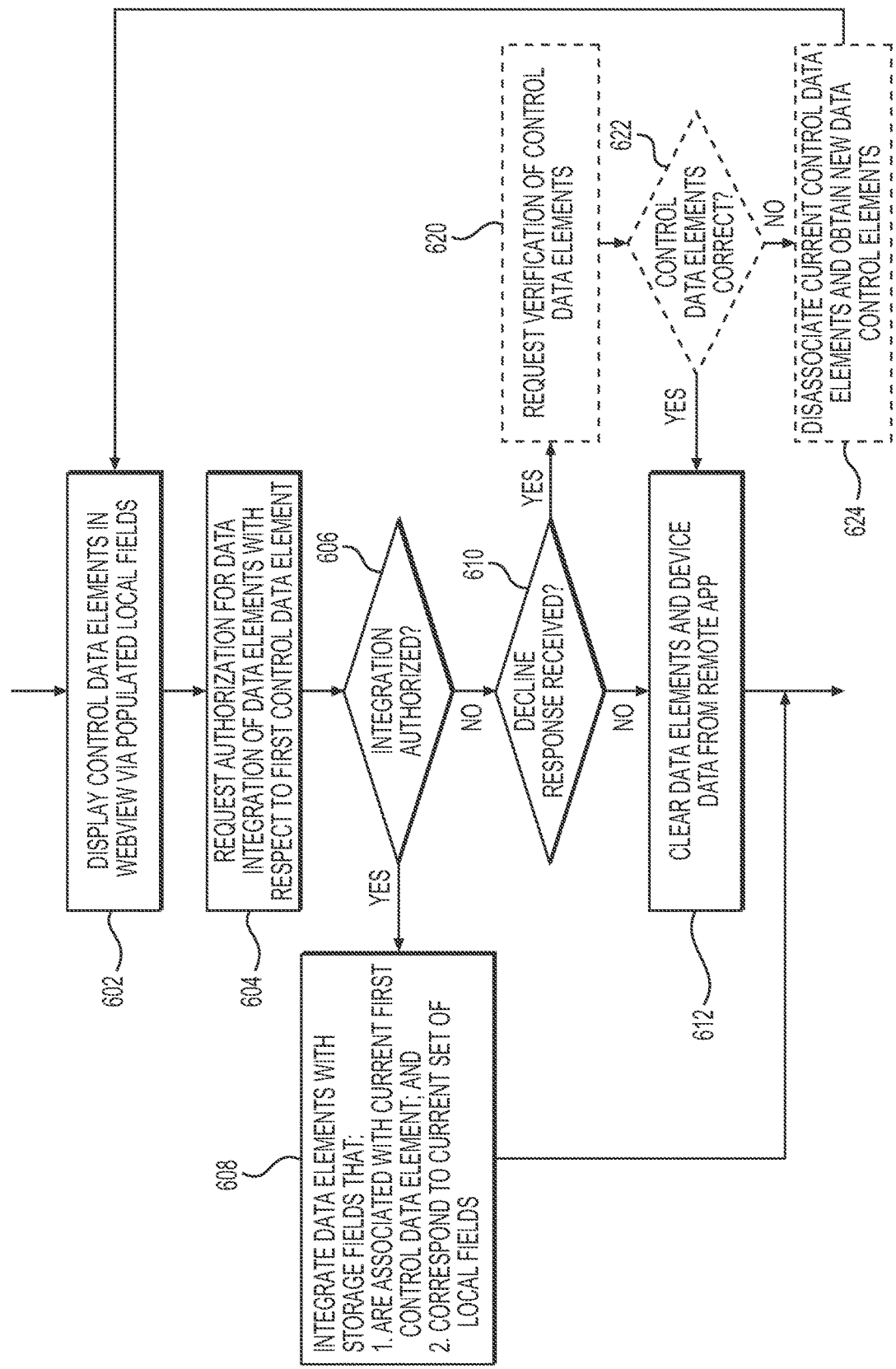
FIG. 6 illustrates an exemplary method of integrating data elements, according to an aspect of the present disclosure.

FIG. 6 illustrates an exemplary method of integrating data elements, according to an aspect of the present disclosure. The method of FIG. 6 is directed toward a situation in which prior to stage 602, the remote application 300 has determined that data elements of device data correspond to local fields of a set of local fields in the remote application 300, and have been associated accordingly. Stages 602, 604, and 606 can include all of the processes described herein with regards to stages 318, 320, and 322 of FIG. 3, respectively. Further, stage 608 can include all of the processes described herein with regards to stages 324, 326, and 328 of FIG. 3.

Turning to stage 610 of the method, the remote application 300 determines whether a 2nd request result was not received in stage 606, or authorization was declined. In the case of the former, the situation may correspond to a timeout and the remote application 300 can clear the device data in stage 612. In the case of the latter, the method can optionally include the remote application 300 generating a prompt in stage 620 requesting verification of the control data elements associated with current combinations of data elements and local field associations. At stage 622 of the method, the remote application 300 can either communicate with the backend 208 or receive information from an operator and determine if the current control data elements are correct. In the event the control data elements are not correct, in stage 624 of the method, the remote application 300 can disassociate the current control data elements with the current data elements, and obtain new control data elements as described with the method of FIG. 3. Otherwise, the remote application 300 can clear the device data and data elements in stage 612.

Figure 7:
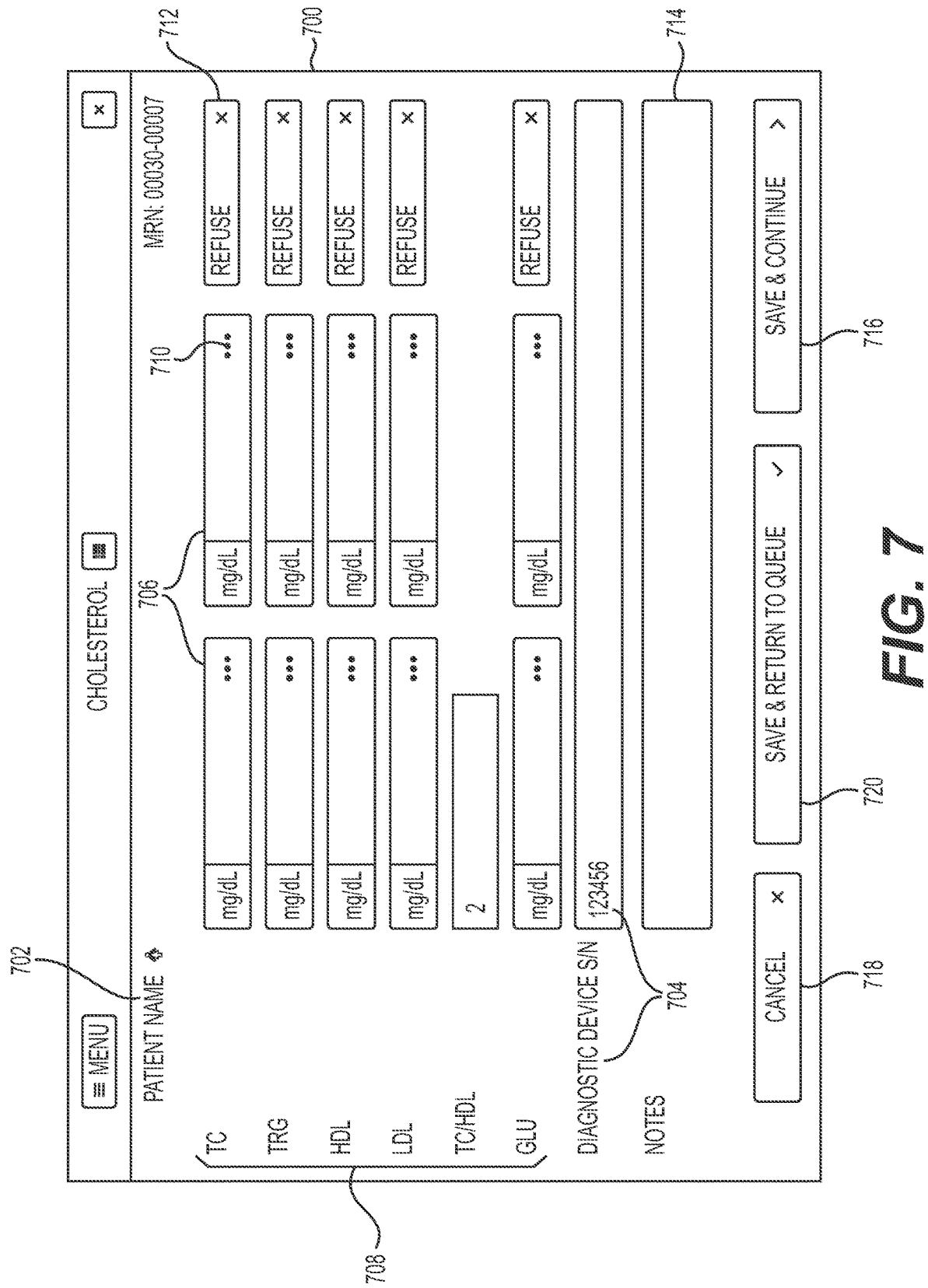
FIG. 7 illustrates an exemplary graphical user interface, according to an aspect of the present disclosure.

FIG. 7 illustrates an exemplary graphical user interface (here after referred to as "GUI 700" or "interface 700"), according to an aspect of the present disclosure. The exemplary GUI 700 can be executed by the remote application 300 which can then be caused to communicate with the backend 208. The interface 700 itself is implemented on the user device 204 by the native application 206 through a respective webview component. The webview component enables the native application 206 to display the interface 700 of the remote application 300, and allow input provided via the user device 204 to be directly input into the remote application 300 without being permanently stored on the user device 204.

The interface 700 of FIG. 7 may track with stage 120 or stages 318 and 320 of the methods described herein. In particular, a first control data element 702 and a second control data element 704 can respectively correspond to a patient and diagnostic device, and may remain after a validation result was displayed on the interface 700 as result of implementations corresponding to stage 114 or stage 310. A set of local fields 706, which are defined by local field identifiers 708, are illustrated in FIG. 7. The local fields 706 are populated with data elements 710. The local field identifiers 708 constitute data which data elements 710 were previously compared to and associated with in implementations by the remote application 300 that may correspond to stage 112 or stage 308.

As illustrated in FIG. 7, the interface 700 includes individual second authorization options 712, such that an operator can define a particular combination of local fields 710 within the set of local fields 710 displayed for second authorization. As such, an operator can determine which data elements may correspond to false positives or diagnostic device error, and only have valid data elements subsequently stored permanently. The interface 700 further includes a comment section 714 in which an operator can input any notes believed to be relevant to an examination of a patient, what the test results (data elements 710) could indicate, or other general information. This information can also be permanently stored in the database of the backend 208 upon the appropriate operation of the remote application 300 and the user interface 700 (via the user device 204) by the operator as follows.

It will be understood that FIG. 7 represents a situation in which the data elements 710 displayed on the user device 204, are temporarily being stored in the script of the remote application 300. However, the data elements 710 are not being permanently stored by the user device 204. The interface 700 includes a second authorization option 716, a decline option 718, and a hold option 720 which can be selected by an operator. Should none of these options be selected within a certain period of time for which the data elements 710 are displayed populating the local fields 706, the remote application 300 may clear the local fields and delete the device data and data elements.

Selection of the second authorization option 716 can result in the data elements 710 that the operator has not removed through selections of respective individual second authorization options 712, being transmitted to the backend 208 along with an integration instruction for permanent storage. The integration instruction may include the remaining data elements 710, and the local field identifiers 708 that the backend 208 may reference to populate storage fields with corresponding data elements. Selection of the decline option 718 may cause the local fields to be cleared and the device data/elements be deleted in one example. In another example, the remote application 300 may generate a series of prompts that request verification and permit the changing of the first and second control data elements 702, 704.

Selection of the hold option 720 may cause the remote application 300 to store the data elements for an additional period of temporary storage time. Should the additional period afforded to the data elements put on hold lapse, the data elements and device data may be discarded. Alternatively, the operator may operate the user device 204 to obtain new device data with new data elements that correspond to a different or the same set of local fields. In one example in which the second authorization option 716 is selected with respect to the new data elements, both the original and new data elements, and respective associations, may be transferred to the backend 208.

Figure 8:
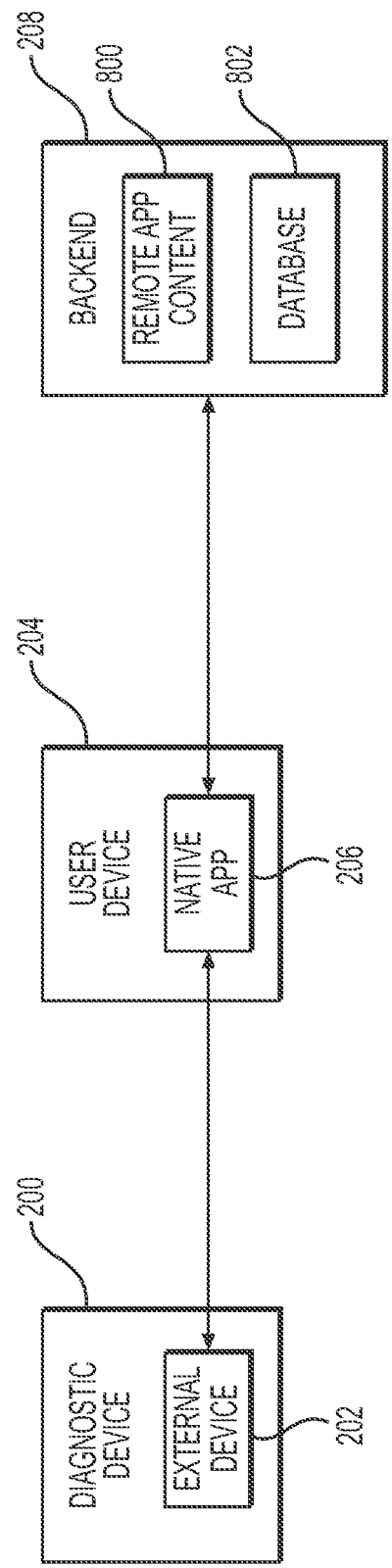
FIG. 8 is an illustration of example components of a system, according to an aspect of the present disclosure.

FIG. 8 is an illustration of example components of a system 800, according to an aspect of the present disclosure. The diagnostic device 200 can be any device used to test and report any biometric parameter. In one example the diagnostic device may be any device (e.g. a CardioChek® analyzer) configured to analyze metabolic blood chemistry panel test strips (lipid panel test strips), an oximeter, a sphygmomanometer, a dedicated glucose meter, a scale, a stadiometer, a thermometer, a heart monitor, or a stethoscope. The external device 202 can be a BLUETOOTH or WIFI component (e.g. adapter) that can be attached and removed from the diagnostic device. In another example, a component such as a BLUETOOTH or WIFI adapter may be incorporated in the diagnostic device. The external device can communicate with the diagnostic device and obtain device data from the diagnostic device 200 including test and measurement results.

The external device 202 may be paired to the user device 204 through a network, and can be any computing device, such as a cell phone, laptop, personal computer, or workstation, and can include a non-transitory, computer-readable medium containing instructions that are executed by a processor in the user device 204. The user device 204 may have installed thereon, the native application 206 which is capable of operating hardware or other components of the user device 204 to access the network, identify the external devise 202, pair the user device 204 to the external device 202, and establish a data channel therebetween. In addition, the native application 206 can access the same or different network, such as the internet or web browser of the internet, to communicate with the backend 208 and load the remote application 300.

The backend 208 can be a server, computing device, or network of multiple servers or computing devices, having one or more processors and memory stores. Content for the remote application 300 may be maintained on the backend 208, and supplied to the native application 206 by a remote application content supplying component 800 ("content component 800") for the backend 208. In one example, the content component 800 is a web server, or functions as web server within a server that embodies the backend 208. Accordingly, the native application 206 can communicate with the content component 800 of the backend 208 to load the remote application 300 on the user device 204 in a respective webview component. The remote application 300 so loaded, may receive device data and determine whether the device data includes any data elements that correspond to local fields thereof.

The backend 208 further can include a database 802 that maintains storage fields as described herein. Thus, the database 802 can store data elements in storage fields grouped into patient records; each patient record being associated with at least one control data element that corresponds to a particular patient.

It will be appreciated that the foregoing description provides examples of the disclosed integration system. These examples given above are merely illustrative and are not meant to be an exhaustive list of all possible designs, aspects, applications or modifications of the disclosure. Further, it is contemplated that other implementations of the disclosure may differ in detail from the foregoing examples. All references to the disclosure or examples thereof are intended to reference the particular example being discussed at that point and are not intended to imply any limitation as to the scope of the disclosure more generally. All language of distinction and disparagement with respect to certain features is intended to indicate a lack of preference for those features, but not to exclude such from the scope of the disclosure entirely unless otherwise indicated.

We claim:

1. A computer-implemented method of securely integrating diagnostic-device-generated device data in a backend through a user device the method comprising:
generating, with a diagnostic device in communication with an external device, an original instance of device data that corresponds to an analysis of a specimen performed by the diagnostic device;
receiving, with a native application of the user device, the device data through the external device;
establishing, with the native application, a secure connection with the backend;
implementing, through the native application and the secure connection, a user interface of a remote application on the user device;
implementing, through the native application, a local data call function of a remote application such that the remote application receives the device data;
determining, by the remote application, a compatibility of data elements of the device data with a first set of local fields of the remote application;
validating, by the remote application, the device data based on the compatibility determined for the data elements and the first set of local fields;
requesting, with the remote application a first authorization to integrate the device data into the first set of local fields based on a result of the validating;
populating, with the remote application, at least one of the first set of local fields with at least one corresponding data element from the device data and associating a first data control element with the data elements according to a first request result received in response to the requesting of the first authorization without permanently storing the device data on the user device;
requesting, with the remote application, a second authorization to integrate the device data, the requesting the second authorization including causing an option being displayed in an inactive state in the user interface of the remote application to be active for selection; and
populating, through the remote application, at least one storage field maintained by the backend for a first time with the at least one corresponding data element based on a selection of the option in response to the requesting of the second authorization, the at least one storage field:
being specific to the specimen and associated with the first data control element on the backend, and
corresponding to the at least one of the first set of local fields,
wherein requesting the first and second authorizations avoids cross-population of patient records associated with the device data in the backend.

2. The computer-implemented method of claim 1, further comprising:
causing the native application to communicate with the remote application and initiate the local data call function in response to establishing the secure connection.

3. The computer-implemented method of claim 1,
wherein implementing the local data call function of the remote application includes the native application transferring the device data to the remote application without the device data being permanently stored by the native application or in a location on the user device.

4. The computer-implemented method of claim 1,
wherein the first set of local fields is expressed in a first page of the user interface of the remote application, and
wherein the remote application includes a plurality of pages and each of the plurality of pages expresses a respective set of local fields.

5. The computer-implemented method of claim 4,
wherein the data call function is a first data call function of the first page and each of the plurality of pages includes a respective data call function, and
wherein the first page is selected from the plurality of pages by the remote application to be loaded in the user interface based on the device data.

6. The computer-implemented method of claim 4, further comprising:
determining, with the remote application, the data elements do not correspond to the first set of local fields based on the compatibility determined for the data elements,
wherein requesting the first authorization includes requesting a different one of the plurality of pages be selected.

7. The computer-implemented method of claim 1, further comprising:
determining, with the remote application, the data elements do not correspond to the first set of local fields based on the compatibility determined for the data elements;
deleting the device data from the remote application based on the determination; and
setting the validation result to indicate the device data has been deleted prior to requesting the first authorization.

8. The computer-implemented method of claim 1,
wherein the device data includes a plurality of print commands interspersed between data elements, and
wherein the remote application extracts the data elements from the print commands as part of determining the compatibility of the data elements and validating the device data.

9. The computer-implemented method of claim 1, further comprising, prior to receiving the device data:
pairing, with the native application, the user device to the external device; and
establishing, with the native application, a data channel between the user device and the external device.

10. The computer-implemented method of claim 1, wherein the diagnostic device is configured to perform a lipid panel test on a blood sample provided on a test strip, and wherein the device data includes results of a lipid panel test performed for a patient identified by the first control data element.

11. A non-transitory, computer-readable medium comprising instructions that, when executed by a processor of a user device, perform stages for securely integrating diagnostic-device-generated device data in a backend through the user device, the stages comprising:
generating, with a diagnostic device in communication with an external device, an original instance of device data that corresponds to an analysis of a specimen performed by the diagnostic device;
receiving, with a native application of the user device, the device data through the external device;
establishing, with the native application, a secure connection with the backend;
implementing, through the native application and the secure connection, a user interface of a remote application on the user device;
implementing, through the native application, a local data call function of a remote application such that the remote application receives the device data;
determining, by the remote application, a compatibility of data elements of the device data with a first set of local fields of the remote application;
validating, by the remote application, the device data based on the compatibility determined for the data elements and the first set of local fields;
requesting, with the remote application, a first authorization to integrate the device data into the first set of local fields based on a result of the validating;
populating, with the remote application, at least one of the first set of local fields with at least one corresponding data element from the device data and associating a first data control element with the data elements according to a first request result received in response to the requesting of the first authorization without permanently storing the device data on the user device;
requesting, with the remote application, a second authorization to integrate the device data, the requesting the second authorization including causing an option being displayed in an inactive state in the user interface of the remote application to be active for selection; and
populating, through the remote application, at least one storage field maintained by the backend for a first time with the at least one corresponding data element based on a selection of the option in response to the requesting of the second authorization, the at least one storage field:
being specific to the specimen and associated with the first data control element on the backend, and
corresponding to the at least one of the first set of local fields,
wherein requesting the first and second authorizations avoids cross-population of patient records associated with the device data in the backend.

12. The non-transitory, computer-readable medium of claim 11, the stages further comprising:
causing the native application to communicate with the remote application and initiate the local data call function in response to establishing the secure connection.

13. The non-transitory, computer-readable medium of claim 11,
wherein implementing the local data call function of the remote application includes the native application transferring the device data to the remote application without the device data being permanently stored by the native application or in a location on the user device.

14. The non-transitory, computer-readable medium of claim 11,
wherein the first set of local fields is expressed in a first page of the user interface of the remote application, and
wherein the remote application includes a plurality of pages and each of the plurality of pages expresses a respective set of local fields.

15. The non-transitory, computer-readable medium of claim 11,
wherein the device data includes a plurality of print commands interspersed between data elements, and
wherein the remote application extracts the data elements from the print commands as part of determining the compatibility of the data elements and validating the device data.

16. The non-transitory, computer-readable medium of claim 11, wherein the diagnostic device is configured to perform a lipid panel test on a blood sample provided on a test strip, and wherein the device data includes results of a lipid panel test performed for a patient identified by the first control data element.

17. A system for securely integrating diagnostic-device-generated device data a backend of the system through a user device, the system comprising:
a diagnostic device;
at least one memory storage including a non-transitory, computer-readable medium comprising instructions; and
the backend,
wherein the diagnostic device and the backend include processors that execute the instructions to carry out stages comprising:
generating, with the diagnostic device in communication with an external device, an original instance of device data that corresponds to an analysis of a specimen performed by the diagnostic device;
causing a user device to receive, with a native application, the device data through the external device;
establishing, with the native application, a secure connection with the backend;
implementing, through the native application and the secure connection, a user interface of a remote application on the user device;
implementing, through the native application, a local data call function of a remote application such that the remote application receives the device data;
determining, by the remote application, a compatibility of data elements of the device data with a first set of local fields of the remote application;
validating, by the remote application, the device data based on the compatibility determined for the data elements and the first set of local fields;
requesting, with the remote application a first authorization to integrate the device data into the first set of local fields based on a result of the validating;
populating, with the remote application, at least one of the first set of local fields with at least one corresponding data element from the device data and associating a first data control element with the data elements according to a first request result received in response to the requesting of the first authorization without permanently storing the device data on the user device;
requesting, with the remote application, a second authorization to integrate the device data, the requesting the second authorization including causing an option being displayed in an inactive state in the user interface of the remote application to be active for selection; and
populating, through the remote application, at least one storage field maintained by the backend for a first time with the at least one corresponding data element based on a selection of the option in response to the requesting of the second authorization, the at least one storage field:
being specific to the specimen and associated with the first data control element on the backend, and
corresponding to the at least one of the first set of local fields,
wherein requesting the first and second authorizations avoids cross-population of patient records associated with the device data in the backend.

18. The system of claim 17, the stages further comprising:
causing the native application to communicate with the remote application and initiate the local data call function in response to establishing the secure connection.

19. The system of claim 17,
wherein implementing the local data call function of the remote application includes the native application transferring the device data to the remote application without the device data being permanently stored by the native application or in a location on the user device.

20. The system of claim 17, wherein the diagnostic device is configured to perform a lipid panel test on a blood sample provided on a test strip, and wherein the device data includes results of a lipid panel test performed for a patient identified by the first control data element.

* * * * *